United States Patent [19]

Raijmakers et al.

[11] Patent Number: 5,998,639
[45] Date of Patent: Dec. 7, 1999

[54] SULFATATION OF ESTROGEN MIXTURES

[75] Inventors: Petrus Hendricus Raijmakers, Uden; Robert Gerrit Hofstraat, Oss; Henricus Petrus Antonius Johannes Maria van den Boom, Volkel, all of Netherlands

[73] Assignee: Akzo Nobel, N.V., Arnhem, Netherlands

[21] Appl. No.: 08/852,625

[22] Filed: May 7, 1997

Related U.S. Application Data

[63] Continuation-in-part of application No. 08/744,513, Nov. 6, 1996, Pat. No. 5,739,363.

[51] Int. Cl.[6] .................................................. C07J 1/00
[52] U.S. Cl. ......................... 552/625; 552/626; 552/630
[58] Field of Search .................................. 552/625, 630, 552/626

[56] References Cited

U.S. PATENT DOCUMENTS

| | | | |
|---|---|---|---|
| 5,210,081 | 5/1993 | Junghans | 514/179 |
| 5,395,831 | 3/1995 | Gemmill et al. | 514/179 |
| 5,739,363 | 4/1998 | Raijmakers | 552/625 |

FOREIGN PATENT DOCUMENTS

| | | |
|---|---|---|
| 0 771 816 A2 | 5/1997 | European Pat. Off. . |
| 0771816 A2 | 5/1997 | European Pat. Off. ........... C07J 1/00 |
| 697531 | 9/1953 | United Kingdom . |

OTHER PUBLICATIONS

R.W. Roos, *Journal of Chromatographic Science*, 14:11:505–512, 1976.

K.M. Mcerlane et al., *Journal of Pharmaceutical Sciences*, 66:4:523–526, 1977.

"FDA Panel—No Decision on Oestrogens", *SCRIP*, 2049:15, 1995.

Ayanoglu et al., *Tetrahedron*, 35:13:1591–1594, 1979.

Jenkins et al. The Preparation and Properties of Steriod Sulfate Esters, Methods in Enzymology, 15, 351–358, 1969.

*Primary Examiner*—Jose' G. Dees
*Assistant Examiner*—Alton Pryor
*Attorney, Agent, or Firm*—Mary E. Gormley

[57] ABSTRACT

The invention relates to a method for the preparation of a mixture of sulfated estrogens containing delta(8,9)-dehydro estrone [delta(8,9)DHE] or derivatives thereof.

4 Claims, No Drawings

SULFATATION OF ESTROGEN MIXTURES

This application is a continuation-in-part of Ser. No. 08/744,513, filed Nov. 6, 1996 now U.S. Pat. No 5,739,363.

FIELD OF THE INVENTION

The invention relates to a method for the preparation of a mixture of sulfated estrogens, more particularly to the sulfatation of a mixture containing 3-hydroxy-estra-1,3,5(10), 8(9)-tetra-en-17-one [delta(8,9)-dehydro estrone; delta(8,9) DHE; delta 8 estrone; 8,9 dehydro estrone; CAS no. 61612-83-7].

BACKGROUND OF THE INVENTION

The sodium sulfate of the delta(8,9) derivative of estrone [delta(8,9)DHES] is present in minor amounts of about 3–4% in natural conjugated estrogen compositions, for instance in the commercially available product Premarin® which is being used in hormone replacement therapy.

In addition to estrone sodium sulfate, several components have been identified in natural conjugated estrogen compositions among others the sodium sulfates of equilin (in amounts of 22.5–30.5%), 17 alfa dihydro equilin (13.3–19.5%), 17 beta dihydro equilin (0.5–4.0%), 17 alfa estradiol (2.5–9.5%) 17 beta estradiol (<4.5%) and delta(8, 9)-dehydro estrone (<12.5%) (U.S. Pharmacopoeia, 1995, p. 627).

It has been suggested in SCRIP no. 2049 (1995), p. 15 that minor amounts of delta(8,9)DHES could have a significant contribution to the effect of conjugated estrogens. It has further been suggested that delta(8,9)DHES, which has a relatively low affinity to the estrogen receptor, has a high functional activity, which may play a role in the reported LDL-cholesterol-reducing properties and cardiovascular effects of conjugated estrogens, in particular of Premarin®. Data reveal that delta(8,9)DHES contributes to about 18% of Premarin's circulating estrogens. It is therefore of importance to obtain an easy method of production of sulfated mixtures of delta(8,9)DHE.

Apart from cumbersome total synthesis, J. C. Jacquesy et al., Chem. Abstr. 76 (1972), 154000f disclosed isomerization of equilin in hyperacidic media. Conversion to delta(8, 9)DHE was achieved by using hydrogen fluoride or hydrogen fluoride/antimony fluoride at −30° C. It is evident that such dangerous reaction conditions are completely unsuitable and unacceptable for large scale production of delta(8, 9)DHE. Moreover, in U.S. Pat. No. 5,395,831, wherein the method of Jacquesy is applied, it has been disclosed that said hydrogen fluoride method does not provide pure delta(8,9) DHE, but in addition thereto 10% of the unwanted delta(9, 11)-isomer. Methods of production which are commercially acceptable, whether or not through isomerization of equilin, thus have not been disclosed.

Synthesis of sulfated esters of steroids has been described in the literature. As summarized by Jenkins and Sandberg (Methods in Enzymology, 15, 351–358, 1969) one of the methods involves the sulfatation of mono- and dihydroxy C-18 and C-19 steroid compounds utilizing pyridine sulfuric acid complexes. This process, however, has been applied to individual, i.e. free from other, steroid compounds. The process according to the present invention has the advantage that in a single reaction mixture sulfated estrogens can be obtained in a specific ratio. It has surprisingly been found that although the estrogens present in the natural conjugated estrogen preparations have different physical properties, such as crystallization behavior and solubility, the ratio of sulfated products in the sulfatation reaction mixture reflects the amounts of the input components. Therefore, a one pot reaction suffices to prepare the sulfated estrogen mixture. In addition, this reaction can, when appropriate, be coupled directly to the isomerization reaction by which delta(8,9) DHE is prepared, i.e. isomerization of equilin or a derivative thereof to said derivative. In this reaction equilin or a derivative thereof is treated with a lithium salt of ethylenediamine or with lithium amide in dimethylsulfoxide.

SUMMARY OF THE INVENTION

Thus, the present invention offers the first easy and inexpensive method of production of sulfated steroid mixtures containing delta(8,9)DHE through sulfatation of an estrogen mixture containing delta(8,9)DHE or derivatives thereof which can be obtained by isomerization of equilin or a derivative thereof.

Accordingly mixtures of estrogens comprising a compound according to the general formula I

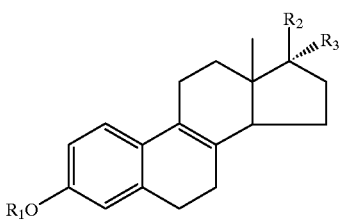

wherein $R_1$ is H,
$R_2$ is H and $R_3$ is O-acyl; or
$R_3$ is H and $R_2$ is O-acyl; or
$R_2$ and $R_3$ together represent O can be sulfated in admixture with one or more compounds taken from the group of compounds of general formula II

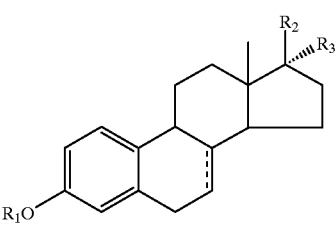

wherein $R_1$, $R_2$ and $R_3$ have the previously defined meanings and the dotted line at position 7–8 represents an optional double bond.

In a preferred embodiment of the invention $R_2$ and $R_3$ in formula I and/or II represent O. More preferably, delta 8,9 estrone is sulfated in admixture with equilin.

According to another embodiment of the invention compounds of general formula II are one or more of the precursors of the minor components as present in natural conjugated estrogen mixtures such as sulfate esters of 17 alfa dihydro equilin, 17 beta dihydro equilin, 17 alfa estradiol and 17 beta estradiol.

The ratio of the compounds in the reaction mixture is not critical but for economical reasons the preferred ratio is the ratio as present in natural mixtures.

DETAILED DESCRIPTION OF THE INVENTION

The compounds of general formula I can be prepared by isomerization of equilin and said derivatives which are indicated in Formula III:

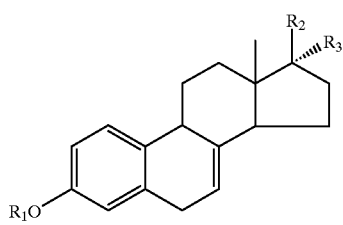

III wherein $R_1$ is silyl(alkyl)$_3$ or O-tetrahydropyranyl, $R_2$ and $R_3$ together represent O; or $R_2$ and $R_3$ together represent acetal or cyclic acetal.

The term alkyl, as used in the definition of the formulas, means a branched or unbranched alkyl group having preferably 1–7 carbon atoms, like hexyl, isobutyl, tertiary butyl, propyl, isopropyl, ethyl, and methyl. Preferably, silyl(alkyl)$_3$ is Si(Me)$_2$tert.butyl. The term acyl means an acyl group derived from an alkylcarboxylic acid, the alkyl moiety having the meaning given previously, or derived from formic acid. Acetals are derived from alcohols having preferably 1–6 carbon atoms.

With the term tetrahydropyranyl also equivalent mixed acetals or mixed hemithioacetals are meant such as e.g. ethoxyethyl, methoxyethyl(MOM), methylmethoxyethyl, methoxyethoxymethyl (MEM), tetrahydrofuranyl, methylthiomethyl, tetrahydrothiopyranyl, tetrahydrothiofuranyl or ethers as methyl and tert-butyl as described in Protective Groups in Organic Synthesis, by Greene, Th. and Wuts, P. (1991), chapter 2, p.14–87.

The isomerization can be performed using lithium salts of ethylenediamine. This method results into the production of very pure delta(8,9)DHE. Such lithium salts can be prepared by treatment of ethylenediamine with lithium or with alkyllithium, preferably with methyllithium. (Co)solvents like tetrahydrofuran, dimethylsulfoxide, and the like may be added. Usually mixtures of derivatives of delta(8,9)DHE and equilin are obtained when (co)-solvents are added. Lithium amide in dimethylsulfoxide (DMSO) also provides mixtures of delta(8,9)DHE and equilin or derivatives thereof, which can be converted according to the present invention into their sodium sulfates, to be used in the manufacture of pharmaceutical compositions containing conjugated estrogens.

Preferably, the C3 position is occupied by a tetrahydropyranyl ether because such an ether can easily be prepared on an aromatic group, is stable under the isomerization conditions, and, after isomerization, can easily be removed to prepare a hydroxyl group for sulfatation.

If $R_1$ in formula III is silyl(alkyl)$_3$, the isomerization is preferably performed at a temperature of between about 0 and 90° C., and with more preference at about 30° C. if equilin or a derivative thereof is treated with a lithium salt of ethylenediamine or about 65° C. if equilin or a derivative thereof is treated with lithium amide in dimethylsulfoxide. If on the other hand, $R_1$ is tetrahydropyranyl a mixture of the substrate and an aforementioned solvent is treated with a lithium salt of ethylenediamine at a temperature of between about −78° C. and 50° C., preferably between approximately 0° C. and −20° C. using THF as the cosolvent.

If the isomerization reaction is performed only partially a mixture of compounds of general formula III and delta 8,9 derivatives is formed which can be further processed to obtain sulfate conjugated estrogens mixtures. Optionally also derivatives of general formula II can be added and in a single reaction all compounds can be sulfated simultaneously. Preferred compounds to be isomerized and sulfated according to the present invention are those wherein $R_2$ and $R_3$ in the formulas represent O.

If in the compound of formula III, $R_1$ is silyl(alkyl)$_3$ or tetrahydropyranyl, the derivatives can be isomerized and subsequently hydrolyzed resulting in compounds according to formula I or a mixture of compounds according to formulas I and III wherein $R_1$ is H by treatment with mild acid such as dilute ($\leq$0.2 N) hydrochloric acid, 50% acetic acid with cosolvents like THF, acetone, methylene chloride, ethanol or by treatment of the derivatives under neutral conditions like trimethylsilyl iodide/trimethylsilyl bromide in methylene chloride; methyl iodide in acetone, $H_2O$, NaHCO$_3$; pyridinium p-toluenesulfonate, tert-butanol; tetrabutylammonium fluoride in methylene chloride; AgNO$_3$ in acetone as described in Protective Groups in Organic Synthesis, by Greene, Th. and Wuts, P. (1991), chapter 2, p.14–87.

The thus obtained estrogen derivative mixture can be sulfated according to the invention in admixture with one or more mono acyl derivatives of the group of 17 alfa dihydro equilin, 17 beta dihydro equilin, 17 alfa estradiol and 17 beta estradiol.

The following examples are illustrative for the invention and should in no way be interpreted as limiting the scope of the invention.

EXAMPLE 1

Lithium (13 g) was added portionwise to 920 ml of ethylenediamine under an atmosphere of nitrogen at 95° C. and the mixture was stirred for 30 min. at 100° C. The reaction mixture was cooled to 23° C., after which 100 g of equilin were added at a temperature of $\leq$30° C. The mixture was stirred for another 2 h at 30° C. The suspension was poured into 2.5 l of ice water and at a temperature $\leq$25° C. acetic acid was added until pH 7. The aqueous layer was extracted three times with 2.5 l of ethyl acetate. The organic layer was washed with water, 5 g of active carbon (Norit®) were added and the suspension was stirred at 21° C. for 30 min. The suspension was filtered over dicalite and the filtrate was evaporated under vacuum until a volume of about 500 ml. The suspension was stirred for 1 h at 0° C., after which the crystalline material was filtered off, washed with ethyl acetate and dried under vacuum at 40° C., to obtain 81 g of delta(8,9)-dehydro estrone, having a purity of about 95%.

The contents of delta(8,9)DHE and equilin were determined using $^1$H-NMR spectroscopy, characteristic peaks of which are 0.90 ppm (C18) for delta(8,9)DHE and 5.53 ppm (C7) and 0.79 ppm (C18) for equilin.

EXAMPLE 2

Lithium amide (5 g) was added to a mixture of 5 g of equilin in 150 ml of DMSO. The mixture was heated to 65° C. and stirred for 70 min. The reaction mixture was poured into 500 ml of water and acidified to pH 6.5 using 4N hydrochloric acid. The crystals were filtered off, washed with water and dried under vacuum at 40° C. to obtain 5 g of a 4:5 mixture of equilin and delta(8,9)-dehydro estrone.

EXAMPLE 3

A 6% solution of methyllithium-lithiumbromide complex in diethylether (23.5 ml) was added during approximately 15 minutes to 46 ml ethylenediamine under an atmosphere of nitrogen at a temperature of approximately 25° C. The temperature of the mixture was raised to 55° C. and diethylether was distilled off. Subsequently the reaction mixture was stirred for 1 h at 55° C. The mixture was cooled to 20° C. and 2.5 g of equilin was added. The mixture was stirred for another 90 minutes at 30° C.

The suspension was poured into ice water and the mixture was extracted with ethyl acetate. After evaporation of the ethyl acetate extract until a volume of 20 ml was reached and cooling to 0° C., 2 g of crystalline delta 8-estrone was isolated.

EXAMPLE 4

Lithium (1,1 g) was added portionwise to 80 ml of ethylenediamine under an atmosphere of nitrogen at 100° C. and the mixture was stirred for 30 min. at 100° C. The reaction mixture was cooled to 23° C., after which 4 g of 17β-dihydroequilin were added at a temperature of ≦30° C. The mixture was stirred for another 4 h at 30° C. The suspension was poured into 250 ml of ice water and at a temperature of ≦25° C. acetic acid was added until pH 7. The suspension was cooled to 5° C. and the crystals were filtered off. The crystals were suspended in 150 ml of water and 100 ml of ethyl acetate were added. The layers were separated and the ethyl acetate solution was evaporated under vacuum until a volume of 20 ml. The suspension was stirred at −15° C. for 1 h, after which the crystals were filtered off, washed with ethyl acetate and dried under vacuum at 40° C., to obtain 2.5 g of 8,9-dehydro-17β-estradiol, having a purity of >95%.

EXAMPLE 5

A solution of methyllithium-lithium bromide (20 ml, 2.1 M) in diethylether was added in 10 min. to 40 ml of ethylenediamine under an atmosphere of nitrogen at 36° C. The temperature of the mixture was raised to 55° C. and diethylether was distilled off. The mixture was stirred for 1 h at 55° C. The reaction mixture was cooled to 3° C., after which 2 g of equilin-3-methylether were added at a temperature of ≦10° C. The mixture was stirred for another 2 h at 12° C., after which 200 ml of ice water were added. To the mixture acetic acid was added until pH 8. The suspension was stirred for 1 h at 15° C., after which the crystals were filtered off, washed with water and dried under vacuum at 45° C., to obtain 2.0 g of 8,9-dehydro-estrone-3-methylether, having a purity of approx. 80%.

EXAMPLE 6

According to the procedure described in example 5, 17β-dihydroequilin 3,17-diacetate, was treated with methyllithium/ethylenediamine at 30° C. to give quantitatively 8,9-dehydro-17β-estradiol having a purity of approx. 90%.

EXAMPLE 7

According to the procedure described in example 4, equilin-17-neopentylacetal was treated with lithium/ethylenediamine at 20° C. to give in a yield of 90% 8,9-dehydro-estron-17-neopentylacetal having a purity of approx. 90%.

EXAMPLE 8

According to the procedure described in example 4, 17β-dihydroequilin-3,17-di(trimethylsilylether) was treated with lithium/ethylenediamine to give quantitatively 8,9-dehydro-17β-estradiol having a purity of approximately 90%.

EXAMPLE 9

To a suspension of equilin (5 g) in 80 ml of methylene chloride were added 13.3 ml of 3,4-dihydro-2H-pyran and 36 mg of p-toluenesulfonic acid at 0° C. The mixture was stirred for 90 min at 0° C., after which 1.3 ml of triethylamine was added. The reaction mixture was washed with water, dried with sodium sulfate and evaporated to dryness. The crude equilin-3-tetrahydropyranylether (6.5 g) was used for isomerization.

EXAMPLE 10

A solution of methyllithium-lithium bromide (8.1 ml, 2.1 M) in diethylether was added in 10 min to 16.2 ml of ethylenediamine under an atmosphere of nitrogen at 36° C. The temperature of the mixture was raised to 55° C. and diethylether was distilled off. The mixture was further stirred for 1 h at 55° C., then cooled to 3° C. After addition of 34.4 ml of tetrahydrofuran the mixture was cooled to −10° C. and equilin-3-tetrahydropyranylether (1.15 g) was added at a temperature of ≦−5° C. The mixture was stirred for another 3 h at −10° C., after which 45 ml of ice water was added. Then, tetrahydrofuran was distilled off using vacuum, and the residual suspension was stirred for 1 h at 15° C. The crystals were filtered off, washed with water and dried under vacuum at 45° C., to yield delta(8,9)-dehydro-estrone-3-tetrahydropyranylether (1.0 g).

EXAMPLE 11

A suspension of 0.73 g of delta(8,9)-dehydro estrone-3-tetrahydropyranylether in acetic acid/acetone/water (4:2:1, 35.7 ml) was heated to reflux and stirred at reflux temperature for 90 min. After cooling to 20° C. 36.5 ml of water was added and the crystalline product was filtered, washed with water and dried under vacuum to yield 0.46 g of delta(8,9)-dehydro-estrone.

EXMAPLE 12

Sulfuric acid (8.2 ml) and acetic anhydride (14.5 ml) were added to pyridine (80 ml) at a temperature <30° C. and under an atmosphere of nitrogen. The mixture was stirred for 1 h at 50° C., when trometamol (0.6 g) was added and the mixture was stirred until it became clear. Delta(8,9)-dehydro estrone (4 g) and 17α-dihydro equilin monoacetate (20.2 g) were added, followed by pyridine (21 ml) and the mixture was stirred for 3 h at 50° C. After completion of the reaction the mixture was cooled to 5° C. and triturated with diethylether (300 ml) which resulted in the formation of an oil and an upper layer. The upper layer was decanted and the residue was dissolved in methanol (375 ml). A solution of sodium hydroxide (12.8 g) in methanol (0.3 l) was added and the mixture was stirred for 2.5 h at reflux temperature. After completion of the reaction, the mixture was cooled to 20° C. and a mixture of n-butanol (0.65 l) and water (0.15 l) was added. Methanol was evaporated in vacuum and the organic layer was washed with aq 5% sodium chloride and water. After evaporation of the organic layer to dryness, the residue was dissolved in 100% ethanol (0.29 l) at 60° C. and the mixture was stirred in the presence of active carbon (0.6 g) for 30 min at 60° C. The suspension was filtered and the filtrate was partially concentrated in vacuum. The solution was cooled to 10° C. and triturated with diethylether (0.27

1). The precipitate was filtered off, washed with diethylether and dried in vacuum to yield 15.5 g of a 1:5 mixture of delta(8,9)-dehydro estrone sodium sulfate and 17α-dihydro equilin sodium sulfate. GLC analysis indicated full recovery of all steroids charged.

EXAMPLE 13

According to the procedure described in example 12, a mixture of delta(8,9)-dehydro estrone (12.5 g) and equilin (12.5 gram) were sulfated with sulfuric acid/acetic anhydride/pyridine. The mixture of crude pyridine sulfates was saponified and converted to the corresponding mixture of sodium sulfates with sodium hydroxide in methanol as described in example 12, yielding 27.5 g of a 1:1 mixture of delta(8,9)-dehydro estrone sodium sulfate and equilin sodium sulfate. GLC analysis indicated full recovery of the steroids charged.

EXAMPLE 14

According to the procedure described in example 12, a mixture of delta (8,9)-dehydro estrone (6.1 g), 17α-dihydro equilin monoacetate (35.8 g), 17β-dihydro equilin monoacetate (3.5 g), 17α-estradiol monoacetate (9.5 g), and 17β-estradiol monoacetate (1.2 g) was sulfated with sulfuric acid/acetic anhydride/pyridine. The mixture of crude pyridinesulfates was treated with sodium hydroxide in methanol and worked up as described in example 12, yielding 44.4 g of a 6:31:3:8:1 mixture of delta(8,9) dehydro estrone sodium sulfate, 17α-dihydro equilin sodium sulfate, 17β-dihydro equilin sodium sulfate, 17α-estradiol sodium sulfate, and 17β-estradiol sodium sulfate. GLC analysis indicated full recovery of all steroids charged.

We claim:

1. A method for the preparation of a mixture of sulfated estrogens, comprising sulfating a compound according the general formula I:

I wherein $R_1$ is H,
$R_2$ is H and $R_3$ is O-acyl; or
$R_3$ is H and $R_2$ is O-acyl; or
$R_2$ and $R_3$ together represent O in admixture with one or more compounds taken from the group of compounds of general formula II

II wherein $R_1$, $R_2$ and $R_3$ have the previously defined meanings and the dotted line at position 7–8 represents an optional double bond, followed by crystallization of the sulfated estrogen mixture.

2. A method for the preparation of a sulfated estrogen mixture, comprising the steps of:
 a. isomerizing compounds with the general formula III

III wherein $R_1$ is silyl(alkyl)$_3$ or O-tetrahydropyranyl,
$R_2$ and $R_3$ together represent O; or
$R_2$ and $R_3$ together represent acetal or cyclic acetal with a lithium salt of ethylenediamine or with lithium amide in dimethylsulfoxide to compounds with general formula I

I wherein $R_1$ is H,
$R_2$ is H and $R_3$ is O-acyl; or
$R_3$ is H and $R_2$ is O-acyl;
or $R_2$ and $R_3$ together represent O;
 b. converting the compounds obtained from step a whereby the $R_1$ substituent becomes H and $R_2$ and $R_3$ together O; and
 c. sulfating the compound obtained from step b in admixture with one or more of 17 alpha dihydro equilin, 17 beta dihydro equilin, 17 alpha estradiol and 17 beta estradiol.

3. The method according to claim 1, wherein $R_2$ and $R_3$ in Formula I and/or III together represent O.

4. The method according to claim 2, wherein $R_2$ and $R_3$ in Formula I and/or III together represent O.

* * * * *

UNITED STATES PATENT AND TRADEMARK OFFICE
CERTIFICATE OF CORRECTION

PATENT NO. : 5,998,639  
DATED : December 7, 1999  
INVENTOR(S) : Raijmakers

Page 1 of 1

It is certified that error appears in the above-identified patent and that said Letters Patent is hereby corrected as shown below:

<u>Title page,</u>
Please add Item -- [30] Foreign Priority Application Data,
Nov. 6, 1995 (EP).......... 95202990.8 --

<u>Column 7,</u>
Line 40, delete claim 1 in its entirety and replace it with the following claim:

1. A method for the preparation of a sulfated estrogen mixture, comprising the steps of:
a. partially isomerizing compounds with the general formula III

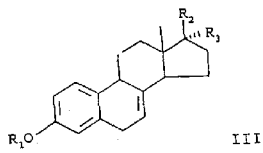

III wherein $R_1$ is silyl(alkyl)$_3$ or o-tetrahydropyranyl;
$R_2$ and $R_3$ together represent O, or
$R_2$ and $R_3$ together represent acetal or cyclic acetal; with a lithium salt of ethylenediamine, optionally in admixture with tetrahydrofuran, or with lithium amide in dimethylsulfoxide to compounds with general formula I

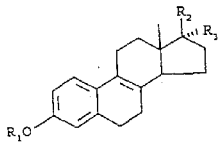

I wherein $R_1$ is H, $R_2$ is H and $R_3$ is O-acyl; or
$R_3$ is H and $R_2$ is O-acyl; or
$R_2$ and $R_3$ together represent O;

b. converting the compounds obtained from step a whereby the $R_1$ substituent becomes H and $R_2$ and $R_3$ together O; and c. sulfating the compounds obtained from step b, optionally in admixture with one or more of 17 alpha dihydro equilin, 17 beta dihydro equilin, 7 alpha estradiol and 17 beta estradiol.

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.      : 5,998,639
DATED           : December 7, 1999
INVENTOR(S)     : Raijmakers It is certified that error appears in the above-identified patent and that said Letters Patent is hereby corrected as shown below:

<u>Title page,</u>
Please add Item -- [30] Foreign Priority Application Data,
Nov. 6, 1995  (EP).......... 95202990.8 --

<u>Column 7,</u>
Line 40, delete claim 1 in its entirety and replace it with the following claim:

```
1.  A method for the preparation of a sulfated estrogen mixture, comprising the steps of:
a.  partially isomerizing compounds with the general formula III
```

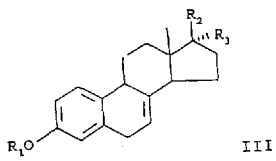

```
                                                    III
```

```
wherein R₁ is silyl(alkyl)₃ or o-tetrahydropyranyl;
R₂ and R₃ together represent 0, or
R₂ and R₃ together represent acetal or cyclic acetal; with a lithium salt of
ethylenediamine,optionally in admixture with tetrahydrofuran, or with lithium amide in
dimethylsulfoxide to compounds with general formula I
```

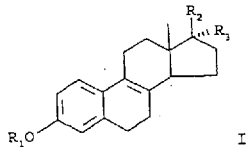

```
                                                     I
```

```
wherein R₁ is H,

R₂ is H and R₃ is O-acyl; or
R₃ is H and R₂ is O-acyl; or
R₂ and R₃ together represent O;

b.  converting the compounds obtained from step a whereby the R₁ substituent becomes H and R₂
and R₃ together O; and c.  sulfating the compounds obtained from step b, optionally in admixture with one or more of
17 alpha dihydro equilin, 17 beta dihydro equilin, 7 alpha estradiol and 17 beta
estradiol.
```

Signed and Sealed this

Twenty-fourth Day of June, 2003

JAMES E. ROGAN
*Director of the United States Patent and Trademark Office*